United States Patent
Danenberg et al.

(10) Patent No.: US 7,336,377 B2
(45) Date of Patent: Feb. 26, 2008

(54) FOOT MEASURING DEVICE

(75) Inventors: Noam Danenberg, Hod Hasharon (IL); Eli Gerby, Netanya (IL)

(73) Assignee: Fitracks Ltd., Ra'anana (IL)

( * ) Notice: Subject to any disclaimer, the term of this patent is extended or adjusted under 35 U.S.C. 154(b) by 0 days.

(21) Appl. No.: 10/583,430

(22) PCT Filed: Dec. 16, 2004

(86) PCT No.: PCT/IL2004/001138

§ 371 (c)(1), (2), (4) Date: Jun. 25, 2007

(87) PCT Pub. No.: WO2005/060782

PCT Pub. Date: Jul. 7, 2005

(65) Prior Publication Data

US 2007/0253004 A1 Nov. 1, 2007

(30) Foreign Application Priority Data

Dec. 22, 2003 (IL) ........................................ 159520

(51) Int. Cl.
*G01B 11/04* (2006.01)
*A43D 1/02* (2006.01)

(52) U.S. Cl. .............................. 356/635; 33/6; 33/512; 33/3 R

(58) Field of Classification Search ................ 356/601, 356/614, 625, 629–636, 639–640; 33/6, 33/512, 515, 3 R, 3 A–3 C See application file for complete search history.

(56) References Cited

U.S. PATENT DOCUMENTS

| 1,725,334 | A |  | 8/1929 | Brannock |
| 5,164,793 | A | * | 11/1992 | Wolfersberger et al. .... 356/607 |
| 5,237,520 | A | * | 8/1993 | White ........................ 382/154 |
| 5,659,395 | A |  | 8/1997 | Brown |
| 6,879,945 | B1 | * | 4/2005 | Cook ............................ 703/2 |
| 7,089,152 | B2 | * | 8/2006 | Oda et al. ................... 702/182 |
| 7,114,260 | B2 | * | 10/2006 | Nguyen et al. ................... 33/6 |
| 2003/0164954 | A1 |  | 9/2003 | Gerhard |

FOREIGN PATENT DOCUMENTS

DE 83 08 980 8/1983

OTHER PUBLICATIONS

International Serach Report for corresponding PCT application—2 pages, Mar. 23, 2005.
International Preliminary Report on Patentability for corresponding PCT application with annexes—12 pages, Dec. 21, 2005.

* cited by examiner

*Primary Examiner*—Sang H. Nguyen
(74) *Attorney, Agent, or Firm*—Roach Brown McCarthy & Gruber, P.C.; Kevin D. McCarthy

(57) ABSTRACT

An apparatus for measuring the dimensions of pairs of human feet and a method for carrying out the measurements using the apparatus is described. The device is based on two light emitter/detector pairs. The emitter/detector pairs are caused to move in mutually orthogonal directions in order to measure the length of the longest foot and the width of each foot in the pair of feet being measured.

12 Claims, 3 Drawing Sheets

FOOT MEASURING DEVICE

FIELD OF THE INVENTION

The present invention is related to the field of measuring human feet for the purpose of determining shoe size.

BACKGROUND OF THE INVENTION

The problem of obtaining accurate foot measurements has existed since man first started to wear shoes. Many devices of varying degrees of complexity have been proposed over the years for providing two-dimensional measurements of length and width of the human foot in order to provide appropriately fitted shoes and insoles. Representative of such devices is that of Charles Brannock, disclosed in U.S. Pat. No. 1,725,334. Brannock's device, familiar to anyone who has ever visited a shoe store, basically consists of two slides mounted on an indexed base plate to determine the length and width of the foot.

Since Brannock's day the technology has improved, providing pressure sensors and light sensitive sensors of various types to measure the length and the width of the foot. In U.S. Pat. No. 5,659,395 is presented a system that improves somewhat on the existing foot measurement systems. The system disclosed in this patent utilizes a combination of a pressure pad assembly for each foot surrounded by a linear array of infrared LEDs located around the perimeter on two sides of each pressure pad and two corresponding arrays of phototransistors acting as detectors on the opposing sides. The length and width measurements are determined by combining information provided by the pressure pad with the data from the infrared arrays indicating which of the optical paths are blocked by the foot placed between the emitters and the receivers. This system additionally has matrices of emitters and corresponding detectors to give height information at selected locations along the perimeter of the foot. The large numbers of LEDS and phototransistors make the measuring apparatus described in U.S. Pat. No. 5,659,395 an expensive device.

The field of retail shoe stores is an intensely competitive one in which each store owner must be able to provide a high level of service in order to achieve and maintain his share of the market. Part of providing such service would be to make available to his customers a system, for measuring their feet and using these measurements to supply good fitting shoes. In order to be able to provide this service, the measuring apparatus must be durable, reliable, and easy to operate; must provide accurate, easy to interpret results; and must be relatively inexpensive to purchase and operate.

It is a purpose of the present invention to provide an apparatus for measuring the length and width of the human foot.

It is another purpose of the present invention to provide an apparatus for measuring the length and width of a human foot that is easy to operate.

It is yet another purpose of the present invention to provide an apparatus for measuring the length and width of a human foot that is relatively inexpensive to purchase and to operate.

Further purposes and advantages of this invention will appear as the description proceeds.

SUMMARY OF THE INVENTION

The apparatus of the invention is meant to provide an accurate but inexpensive solution to the problem of measuring foot size for the purpose of selecting appropriately sized shoes. In order to accomplish this purpose, the apparatus measures each foot separately to determine the maximum width of the pair and measures both feet simultaneously in order to determine the maximum length.

In a first aspect the present invention presents an apparatus for measuring the dimensions of human feet comprising:
- (a) a base, which comprises and supports on its surfaces and within its interior electrical and optical components of said apparatus;
- (b) a cover, which fits over said base to protect said components;
- (c) optical means, which are used to make the measurements of said feet;
- (d) motion causing means, which are used to move said optical means;
- (e) control means, which automatically control the activity of said motion means in order to carry out said measurements;
- (f) counting means, which measure the motion of said motion causing means;
- (g) memory means, which store the results of said counting and, optionally, other information required for the determination of said dimensions;
- (h) computational means, which calculate said dimensions from said results and said information; and
- (i) display means, which display said dimensions and other pre-determined information;

wherein, said cover means comprises internal walls and a bridge which, together with a depression in the upper surface of said base, define the borders of two essentially rectangular wells into which said feet to be measured are inserted in order to carry out said measurements; and wherein, said optical means comprise two light source/detector pairs;

wherein the elements of the first of said pairs are moved by said motion causing means, in a manner synchronized in both time and position, along parallel axes located respectively on two opposing sides of said wells; and wherein the elements of the second of said pairs are moved by said motion causing means, in a manner synchronized in both time and position, along parallel axes located respectively on the other two opposing sides of said wells.

In the preferred embodiment of the apparatus of the invention the light sources are infrared emitting light emitting diodes, the detectors are infrared sensitive phototransistors, the motion causing means comprise two motors each of which drives two belts. Preferably the motors are stepping motors, the counting means count the steps of the stepping motors, and the belts are timing belts.

The control means, counting means, memory means, computation means, and the display means can be an integral part of the apparatus or at least a part of them can be provided in a separate computation unit, for example a personal computer, that is not an integral part of the apparatus.

In another embodiment the apparatus of the invention further comprises a pad comprised of a matrix of pressure sensors that covers the floor of the wells.

In another aspect the present invention provides a method for automatically measuring the maximum length and width of the feet of a human. The method comprises the following steps:

(i) providing an apparatus of the invention;
(ii) placing the feet in the wells with the back of the heel of each foot pressed against the inner wall section of each of said wells and the interior side of each foot pressed against the side of the bridge;
(iii) pressing the start switch initiating the measurement process;
(iv) activating the light source for making the length measurement;
(v) activating the motor to move the light source/detector pair for making the length measurement;
(vi) counting and storing the number of steps of said motor from the "home" position until the signal from said detector disappears as a result of the feet blocking the optical path;
(vii) computing the maximum length of the feet from said counts;
(viii) turning off the light source for making the length measurement;
(ix) activating the light source for making the width measurements;
(x) activating the motor to move the light source/detector pair for making the width measurements;
(xi) counting and storing the number of steps of said motor between the first disappearance and first reappearance and between the second disappearance and second reappearance of the signal from said detector resulting from the feet blocking the optical path;
(xii) computing the width of each foot from said counts;
(xiii) turning off the light source for making the width measurement;
(xiv) causing said motors to be activated moving the attached optical elements until a limit switch is contacted stopping the motion at the "home" position;
(xv) sending length and width measurements to the computational means; and
(xvi) displaying the results of the measurements.

In alternative embodiments of the method of the invention the width measurements can be carried out before the length measurements, or the width and length measurements can be carried out simultaneously. In the preferred embodiment of the invention, the start switch is located on the computation unit, e.g. a personal computer which sends signals to the elements of the system and receives signals from the sensors to automatically carry out all steps of the measuring process up to the final stage of displaying the results.

All the above and other characteristics and advantages of the invention will be further understood through the following illustrative and non-limitative description of preferred embodiments thereof, with reference to the appended drawings.

DETAILED DESCRIPTION OF THE PREFERRED EMBODIMENT

Figure 1:
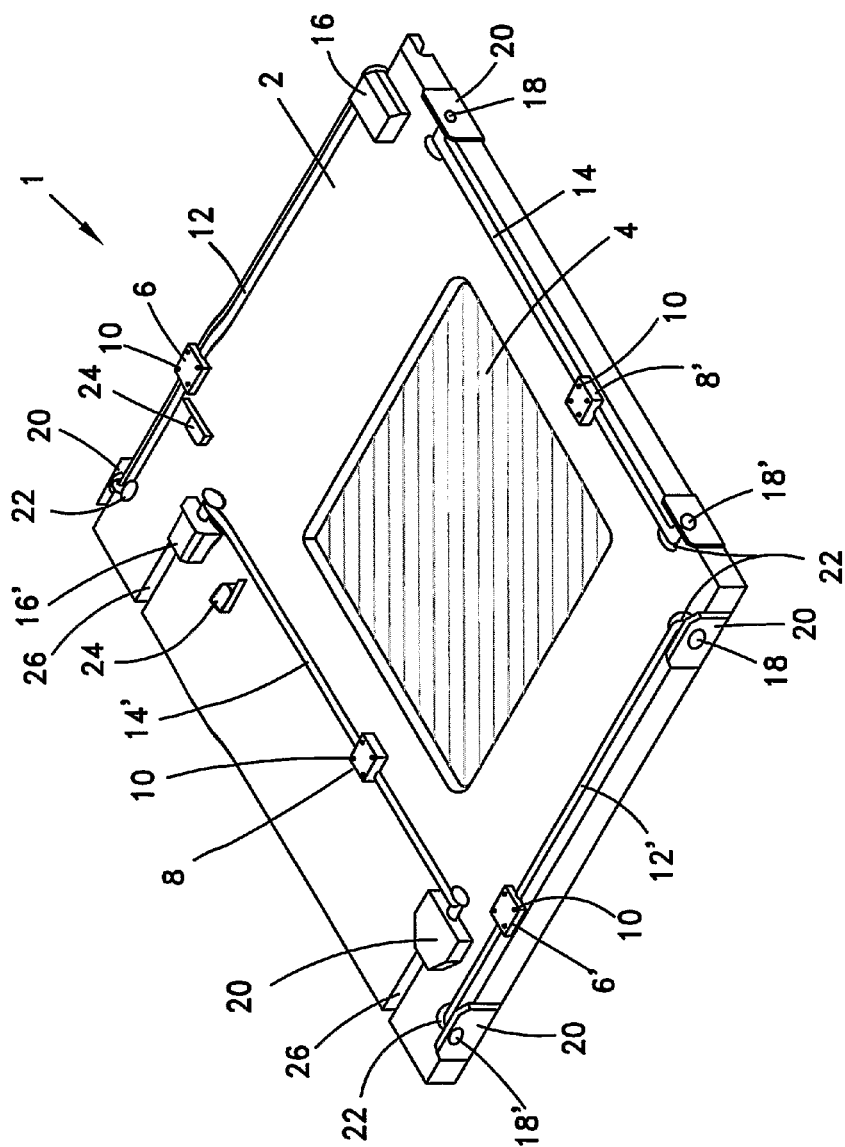
FIG. 1 is a perspective view showing the interior of a preferred embodiment of the measuring apparatus of the invention.

FIG. 1 is a perspective view showing the interior of a preferred embodiment of the measuring apparatus of the invention. The base 1 of the measuring apparatus is comprised of a low housing 2 built of a suitable material such as a metal or an impact resistant plastic. In the preferred embodiment of the invention the housing is fabricated from aluminum. The housing contains and supports on its surfaces and within its interior the electrical and optical components of the apparatus. On the top surface of the housing is created depression 4 into which the feet to be measured are placed.

The length measurement is carried out optically by means of light source/detector pair 6,6' and the width measurements are carried out optically by means of a second light source/detector pair 8,8'. The light source can be of any type capable of producing a well-defined beam of light of sufficient intensity to be detected and differentiated from the ambient light. Having selected the light source, the detector can be of any type having sufficient sensitivity in the spectral range of the light emitted by the source. The light source and the detector may, if necessary, comprise optical elements for collimating or focusing the beam of light. In the preferred embodiment of the apparatus of the invention the light sources are infrared light emitting diodes (LEDS) and the detectors are infrared sensitive phototransistors.

The light sources and detectors are mounted inside hollowed out blocks 10 that are mounted on "endless" belts 12, 12', 14, 14'. The belts are caused to move by rotation of motors 16 and 16'. In the preferred embodiment of the invention, the motors are 12V stepping motors and the belts are off-the-shelf timing belts. At one end, the belts are fitted over pulleys 22 that are mounted directly on the shafts of the motors and at the other end they are fitted over similar pulleys 22 that are mounted on axels that are parallel to and spaced apart from each of the motor shafts. The free ends 18 of the motor shafts and the ends 18' of the axels are supported by suitable support means 20. Preferably, the pulleys are cogged wheels and the support means comprise balls bearings or other rotating elements to reduce friction.

On the right side of motor 16 is mounted the pulley over which is fitted one end of belt 12. On the other side of motor 16, the shaft extends the length of the base 1 of the measuring apparatus, the end 18' of the shaft being visible at the lower part of the left hand side of base 1. At this end is mounted the pulley 22 over which is fitted one end of belt 12'. At the other side of the base (located inside its interior so that it is not visible in FIG. 1) is an axel supported by bearing means such that it can rotate freely about its longitudinal axis. The axel is oriented essentially parallel to the shaft of motor 16 and at each of its ends is attached a pulley over which belts 12 and 12' are fitted respectively. With this arrangement, operation of the motor 16 causes both belts 12 and 12' to move together assuring that the elements of the light source/detector pair 6,6' will always be opposite each other, i.e. that the beam of light will always fall on the face of the detector. A similar discussion explains *mutandis mutatis* how motor 16' causes the motion of light source/detector pair 8,8' to be synchronized with respect to both time and position.

Also shown in FIG. 1 are two limit switches 24, whose function will be described hereinbelow, and two slots 26, which are necessary for attaching and adjusting the belt. Not shown in the figure are the electronic connections, wires, cables, etc. and the internal CPU used to control the operation of the apparatus. Preferably, the apparatus is connected to an external device, such as a personal computer (PC), which may contain some, or all of the software for operating the apparatus, receiving the tracking signals indicating the position of the optical elements and the signals from the detectors, calculating the positions of elements when the detector signals disappear and appear and from these calculations the length and width of the object being measured, and finally displaying the results. Optionally, some or all of the operations described as being performed by an external PC can be performed by computing and display means built into the apparatus.

In order to make a measurement, the motors 16,16' are activated moving the blocks 10 until the blocks containing elements 6 and 8 contact the respective limit switches 24. When the limit switch is contacted, the rotation of the motor is stopped and the measuring system is in its "home" position. The motors are then activated to begin the measurements. If an opaque object is placed in depression 4, then, when the light beam reaches the first edge of the object, the detector will no longer detect the light and the signal sent from the detector to the processing unit will cease. When the block travels past the end of the object, the beam will be unblocked and the signal will resume. As described hereinabove, the signals are all transferred to either the internal CPU and/or the external PC which determines the length of travel of a given detector from the "home" position to when the optical signal first disappears and between the appearance and subsequent disappearance of the optical signal by electronically counting the steps taken by the stepping motor between the when the and again when the sign reappears.

Figure 2:
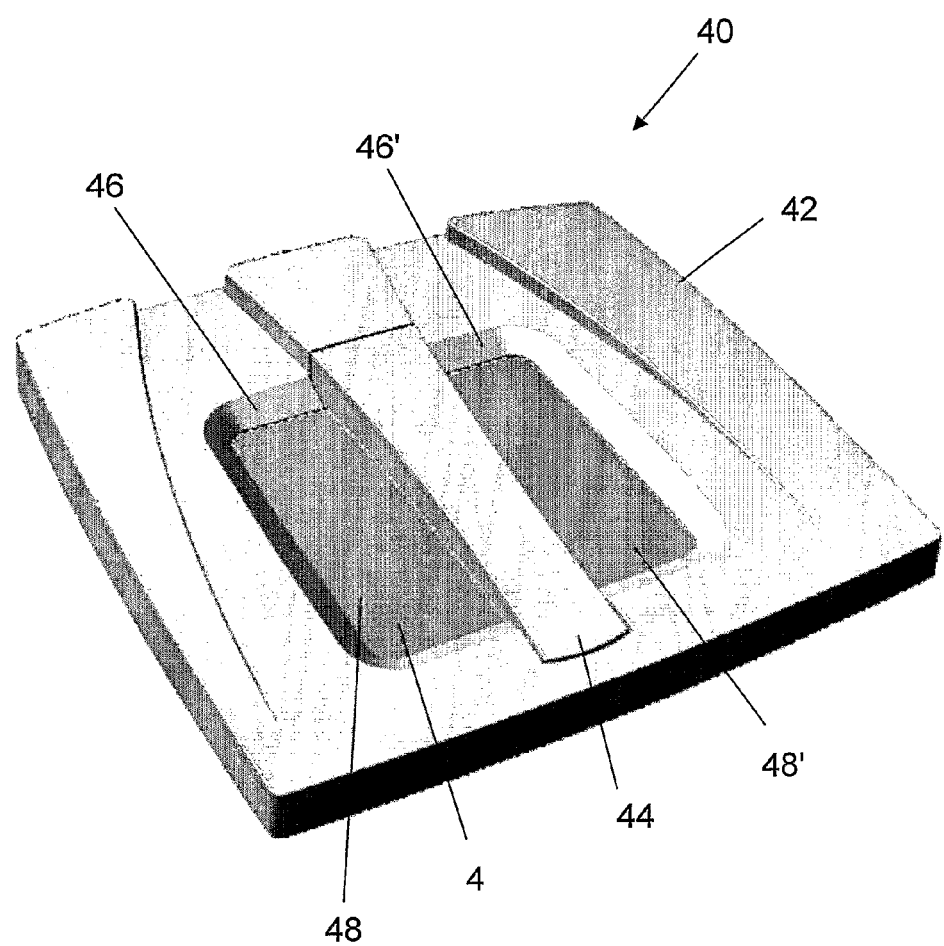
FIG. 2 is a perspective view showing an external view of a preferred embodiment of the apparatus of the invention.

FIG. 2 is a perspective view showing an external view of a preferred embodiment of the apparatus of the invention 40. A cover 42 made of a suitable material such as an impact resistant plastic is fitted over the base 1. The cover has an open area in its interior that essentially matches the shape and dimensions of depression 4 in base 1. A bridge element 44 together with the interior wall sections 46 and 46' of the front of the cover define two essentially rectangular wells 48, 48' into which the right and left feet to be measured are placed respectively. A small gap exists between the bottoms of wells 48, 48' and the lower part of the interior walls of the cover and the bottom of the bridge to allow unobstructed passage of the light beams from source to detector in the absence of any object in one or both of the wells.

For purposes of fitting a pair of shoes, it is not necessary to measure each foot separately but only to determine the maxim length and width of the feet that constitute the pair. The person whose feet are to be measured simply removes his/her shoes and (optionally) stockings and steps into wells 48, 48'. The feet are placed in the wells with the back of the heel of each foot pressed against wall section 46 or 46' and the interior side of each foot pressed against the side of bridge 44. This foot placement is essential to assure alignment of the principle axes of the foot with the directions of motion of the source/detector pairs. The start switch is now pressed initiating the measurement process. First the motor that moves source/detector pair 6,6' is activated to measure the length. Initially there is no obstacle between the source and the detector and only when the tip of the toe of the longest foot is reached is the beam blocked. The number of steps of the stepping motor between the "home" position and the position at which the signal from the detector disappears is counted and stored. Multiplying the stored number of steps by the known distance moved by the block 10 per step gives the length of travel of the source/detector pair 6,6'. Subtracting this distance from the length of the well gives the maximum length of both feet. Now the motor that moves source/detector pair 8,8' is activated. The number of steps until the detector signal first disappears, indicating that the right edge of the right foot has been reached are counted and stored, the motor continues to turn and the steps are counted until the signal returns at the left side of the right foot. The beam is now unblocked for a distance equal to the width of the bridge until the right side of the left foot is reached. The signal disappears and the steps of the motor are counted until the signal reappears at the left side of the left foot. From the known dimensions of the wells and the counts of the steps of the motor the width of each of the feet is separately determined. The maximum value of the two measurements is used to determine the required shoe size. The results of the measurements appear on the display and can appear in many forms including, but not limited to: the maximum measurements expressed in centimeters or inches, the recommended shoe size, and additional information such as pictures of appropriately sized shoes of different types that are either available in the inventory of the store or can be ordered for home delivery.

In another embodiment, a pad comprised of a matrix of pressure sensors is incorporated into the apparatus of the invention. The pad covers the floor of the depression in the base of the apparatus and the software of the apparatus is adapted as required to include the results of the pressure measurements to give additional diagnostic information.

In the preferred embodiment of the invention, after the person whose feet are to be measured steps into the wells of the device, aligns his/her feet, and the start button on the computer is pushed all of the measuring process until the final results are displayed is carried out automatically under control of the computer which sends commands to the activate the various elements at the appropriate time and receives the return signals from the sensors which are either used immediately to guide the process or stored for later use when required.

Figure 3:
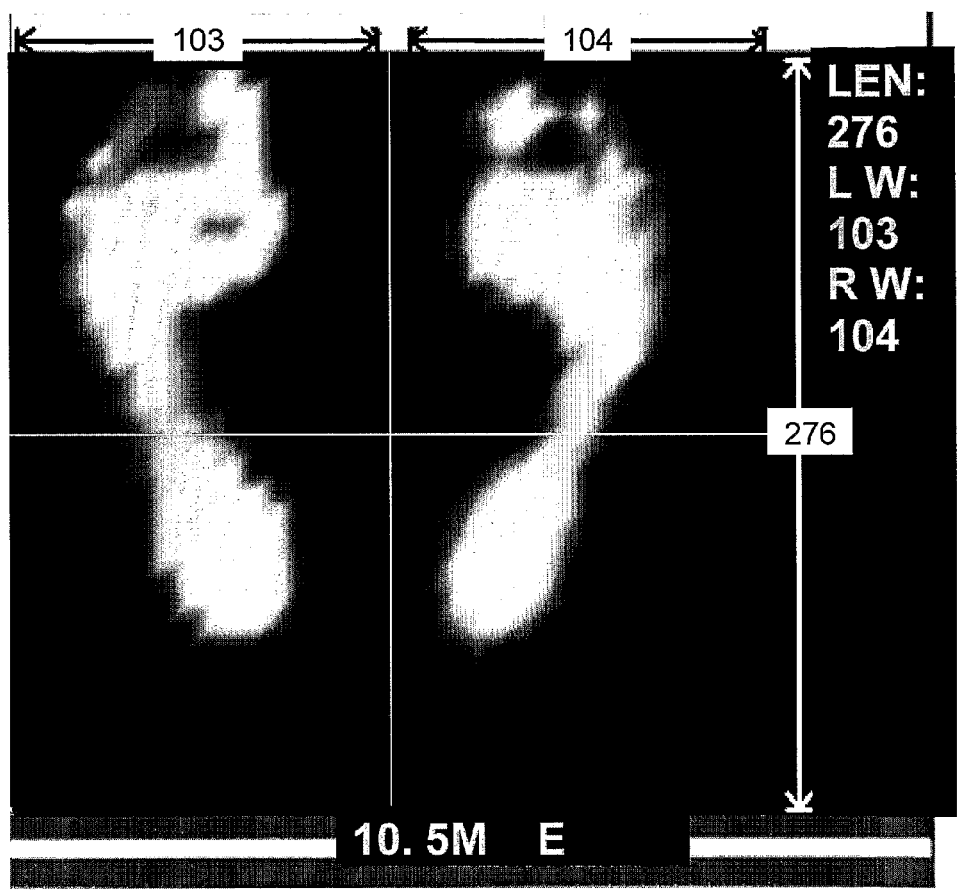
FIG. 3 is a reproduction of a display screen showing the results of a measurement taken with the apparatus of the invention.

FIG. 3 is a reproduction of a display screen showing the results of a typical measurement taken with the apparatus of the invention. The measurements took approximately 20 seconds to perform and have an accuracy of ±1 mm.

The results of the optical measurements are displayed on the top and left margins. The recommended shoe size is on the bottom. It is to be noted that the difference between the heel to toe length of the recommended size and the next smallest shoe size is 0.47 mm, well above the measuring accuracy of the apparatus. Thus it can easily be see that the goal of achieving easy, fast, and accurate foot measurements for the purpose of fitting shoes has been achieved.

It will be easily understood by the skilled person that, although embodiments of the invention have been described by way of illustration, the invention may be carried out with many variations, modifications, and adaptations, without departing from its spirit or exceeding the scope of the claims. For example, the measurement of each foot can be carried out separately to allow the manufacture of custom made shoes if required and the measurements can be carried out in a different order than that described above, including making the length and width measurements simultaneously.

The invention claimed is:

1. An apparatus for measuring parameters of human feet for purpose of determining an appropriate shoe size for said feet, said apparatus comprising:
   (a) a base, which supports components of said apparatus, that are necessary to carry out measurements and comprises a depression in its upper surface into which said feet are placed when said measurements are carried out;
   (b) a cover, which fits over said base to protect said components, said cover comprising an open area in its interior that essentially matches shape and dimensions of said depression in the upper surface of said base, interior walls, and a bridge element all of which, together with said depression in the upper surface of said base, define borders of two essentially rectangular wells into which said feet to be measured are inserted in order to carry out said measurements;
   (c) a pressure pad comprised of a matrix of pressure sensors that covers the floor of said wells;
   (d) two stepping motors, each of when activated, causes a pair of endless belts to move, wherein one end of the first of said belts is fitted over a first pulley located on a shaft projecting out from a first side of said motor and one end of the second of said belts is fitted over a second pulley located on said shaft projecting out from the opposite side of said motor;
   (e) a light source/detector pair attached to each of said pairs of endless belts, wherein one member of each of said light source/detector pair is attached to said first belt and the other member of said light source/detector pair is attached to said second belt;
   (f) control means which controls the activation of said stepping motors;
   (g) counting means which count the steps of the rotation of said shafts of said stepping motors;
   (h) memory means, which store the results of said counting, the signals from said pressure sensors, and other information required for the determination of said parameters;
   (i) computational means, comprising software for computing the length and width of each of said feet from the data supplied by said counting means, and for determining diagnostic information from said sensors in said pressure pad; and
   (j) display means, which display said parameters, and other pre-determined information, wherein each member of each of said light source/detector pair is attached to its respective belt such that proper optical alignment allowing the detector of each of said pairs to detect light emitted from the source of said pair is established and maintained when said belts move;

activation of the first of said stepping motors causes the elements of the first of said light source/detector pairs to move, without disturbing said optical alignment, back and forth along lines that are essentially parallel to the longitudinal symmetry axis of said wells;

activation of the second of said stepping motors causes the elements of the second of said light source/detector pairs to move, without disturbing said optical alignment, back and forth along lines essentially parallel to the transverse symmetry axis of said wells; and said software in said computational means integrates the results of said computed length and width of the feet with said diagnostic information obtained from said pressure pad to determine said appropriate shoe size for each said feet.

2. An apparatus according to claim 1, wherein the light sources are infrared emitting light emitting diodes.

3. An apparatus according to claim 1, wherein the detectors are infrared sensitive phototransistors.

4. An apparatus according to claim 1, wherein the belts are timing belts.

5. An apparatus according to claim 1, wherein the control means, counting means, memory means, computation means, and the display means are an integral part of said apparatus.

6. An apparatus according to claim 1, wherein the control means, counting means, memory means, computation means, and the display mens are provided by a separate computation unit that is not an integral part of said apparatus.

7. An apparatus according to claim 6, wherein the separate computation unit is a personal computer.

8. A method for using the apparatus of claim 1, to measure the maximum length and width of the feet of a human and to determine the appropriate shoe size for said pair of feet, said method comprising the following steps:
   (i) providing an apparatus as defined in claim 1;
   (ii) placing the feet in the wells with the back of the heel of each foot pressed against the inner wall section of each of said wells and the interior side of each foot pressed against the side of the bridge;
   (iii) pressing a start switch activating the sensor in the pressure pad and initiating the measurement process;
   (iv) activating the light source for making the length measurement;
   (v) activating the control means to activate the first motor, thereby moving the light source/detector pair for making the length measurement;
   (vi) activating the counting means and memory means, thereby counting and storing the number of steps of said first motor from the "home" position until the signal from said detector disappears as a result of the longest foot blocking the optical path and sending the data to the computing means;
   (vii) computing the length of the longest foot:
   (viii) turning off the light source for making the length measurement;
   (ix) activating the light source for making the width measurements;
   (x) activating the second motor to move the light source/ detector pair for making the width measurements;

(xi) counting and storing the number of steps of said motor between the first disappearance and first reappearance and between the second disappearance and second reappearance of the signal from said detector resulting from the feet blocking the optical path and sending the data to the computing means;

(xii) computing the width of each foot;

(xiii) turning off the light source for making the width measurement;

(xiv) causing said motors to be activated moving the attached optical elements until a limit switch is contacted stopping the motion at the respective "home" position of each motor;

(xv) sending the signals from the sensors in said pad to the computing means, combining them with the length and width measurements in order to determine the most appropriate shoe size, and sending at least some this information to the display means; and (xvi) displaying the results of the measurements.

9. A method according to claim 8, wherein step (vii) and step (xii) are carried out after step (xiv).

10. A method according to claim 8, wherein steps (iv) to (viii) are carried out simultaneously with steps (ix) to (xiii).

11. A method according to claim 8, wherein steps (ix) to (xiii) are carried out before steps (iv) to (viii).

12. A method according to claim 8, wherein the start switch is located on the computation unit and all steps of said method after step (iii) are carried out automatically under control of said computation unit.

\* \* \* \* \*